United States Patent [19]

Clouser et al.

[11] 4,185,490
[45] Jan. 29, 1980

[54] PHASE DISCRIMINATION IN MODULATED THERMAL CONDUCTIVITY DETECTOR

[75] Inventors: David E. Clouser, Claymont, Del.; John S. Craven, West Grove, Pa.

[73] Assignee: Hewlett-Packard Company, Palo Alto, Calif.

[21] Appl. No.: 949,312

[22] Filed: Oct. 6, 1978

[51] Int. Cl.² .................................. G01N 31/08
[52] U.S. Cl. .............................. 73/23.1; 73/27 R
[58] Field of Search ............ 73/23, 23.1, 27 R, 204; 23/232 C; 422/89

[56] References Cited
U.S. PATENT DOCUMENTS

| 2,255,551 | 9/1941 | Willenborg | 73/27 R |
| 3,967,492 | 7/1976 | Allington | 73/190 R |
| 4,140,396 | 2/1979 | Allington | 73/190 R |

Primary Examiner—Stephen A. Kreitman
Attorney, Agent, or Firm—Donald N. Timbie

[57] ABSTRACT

A thermal conductivity detector in which sample gas and reference gas are made to alternately flow through a thermal conductive cell at a given switching frequency and in which the output signal is applied to a synchronous detector wherein it is mixed with a control wave that is in phase quadrature with the flow component of the output signal.

4 Claims, 3 Drawing Figures

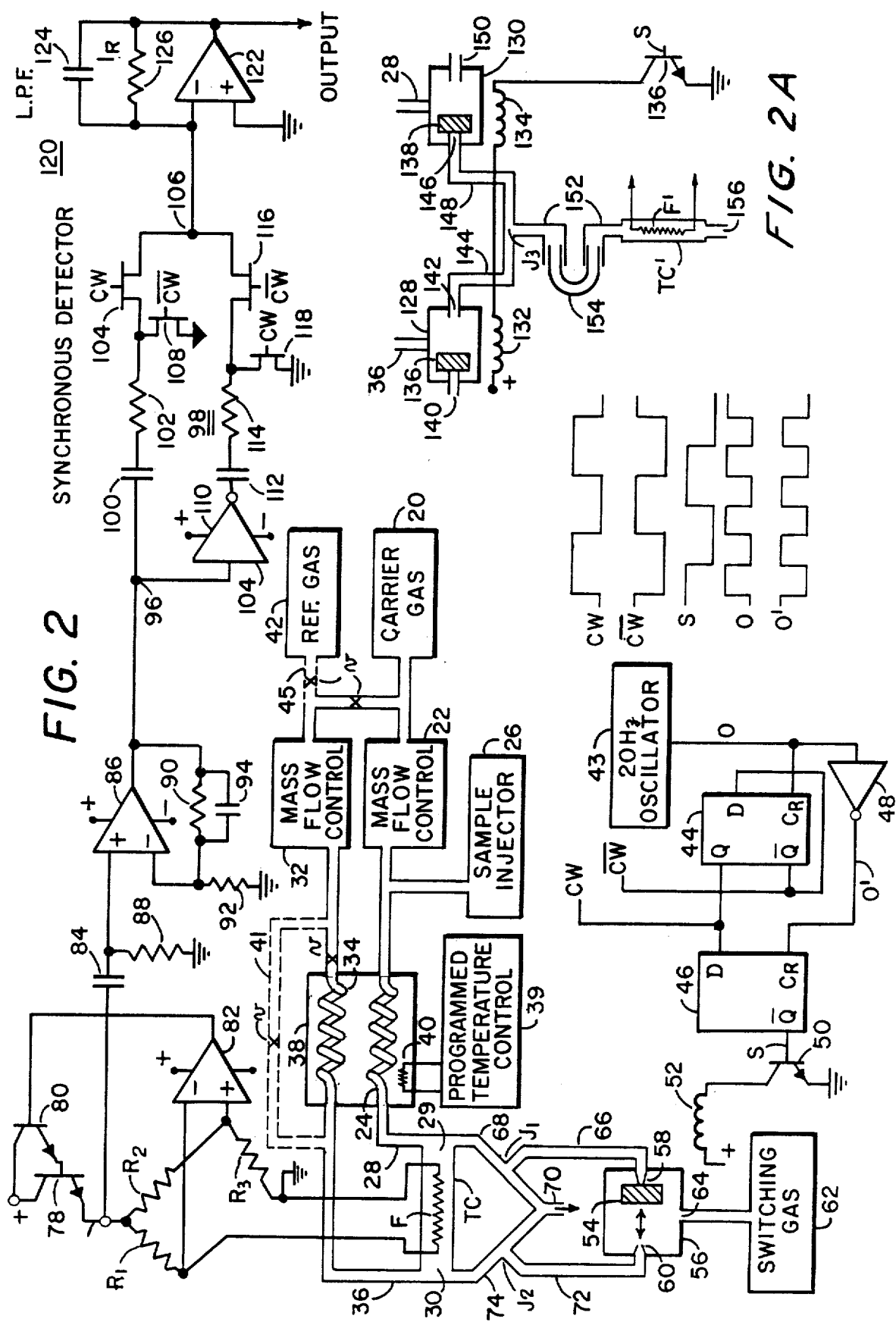

PHASE DISCRIMINATION IN MODULATED THERMAL CONDUCTIVITY DETECTOR

BACKGROUND OF THE INVENTION

Gas chromatographs are used to measure the quantities of various chemicals in a mixture. A sample of the mixture is injected in gaseous form into a stream of carrier gas as it is about to enter a chromatographic column. The various chemicals take respectively different amounts of time to pass through the column so that they appear as sequential concentrations in the stream of carrier gas flowing out of the column. A detector is coupled to the output of the column so as to provide an output signal having a value known as a "baseline value" when carrier gas is emerging from the column and a value that changes with the degree of concentration of each sample gas as it emerges from the column so as to form peaks. By integrating the area between each peak and the baseline, the amount of the corresponding chemical in the injected sample can be determined.

Thermal conductivity detectors are widely used to provide the output signal referred to. In their simplest form, they are comprised of a cell having an electrically heated filament suspended in a cavity. As the output from the column flows through the cavity, the rate at which heat flows from the filament to the wall of the cavity varies with the thermal conductivities of the gases in the cavity. The thermal conductivity of the carrier gas differs from the thermal conductivities of the sample gases, and the thermal conductivities of the sample gases mixed with carrier gas vary with the concentration of the sample gas in the carrier gas. Means are provided for deriving a signal that varies with the rate of heat flow. Accordingly, an output signal of the cell has a baseline value when carrier gas is flowing through its cavity and peaks when the concentrations of the respective sample gases are flowing through the cavity. The output signal is the voltage required to keep the filament at a constant temperature.

One of the problems encountered with such detectors is that the heat flow between the filament and the wall of the cell is directly affected by the temperature of the wall. For this reason it has been customary to reduce the effect of ambient temperatures on the temperature of the wall by imbedding the cell in a large block of aluminum. Even better results are achieved by imbedding two cells in the block, passing carrier gas through one, passing the elutant from the column through the other, and connecting the filaments in a bridge circuit. Thus, if an ambient temperature change causes the wall of each cell to vary in like manner, its effect will be balanced out by the bridge. Either construction is expensive and requires several hours after the application of power to the filament to achieve sufficient thermal equilibrium for accurate readings.

In our U.S. patent application, Ser. No. 730,559, filed on Oct. 7, 1976, and entitled "Modulated Fluid Detector", a single cell thermal conductivity detector is described that is inexpensive and capable of attaining accurate readings within minutes after power is applied to the filament. The cavity of the cell is switched at a given frequency from the output of the column to a source of reference gas so that its output signal, i.e., the voltage required to keep the filament at a given temperature, varies between a value determined by the thermal conductivity of the gas eluting from the column and a value determined by the thermal conductivity of the reference gas. The switching frequency is such that a number of switching cycles occur during the elution of each peak of sample gas from the column. The alternating voltage V thus produced is AC coupled to a synchronous detector wherein it is mixed with a control voltage that is in phase with the switching of the cavity of the cell from the column to the source of reference gas. In this detector, the temperature of the wall of the cell can be permitted to follow the ambient temperature because it changes so slowly with respect to the switching frequency as to have the same effect on the amplitude of the output signal of the cell whether gas from the column or reference gas is flowing through the cell cavity. The synchronous detector derives a signal proportional to the difference between the level of the output signal of the cell under these two conditions so that the effect of variation in the temperature of the cell wall is eliminated. Thus, instead of imbedding the cell in a block of metal, it can be imbedded in a small inexpensive wafer of ceramic material. Furthermore, accurate readings can be attained within a matter of minutes because it is not necessary to wait for thermal equilibrium to be established.

BRIEF DISCUSSION OF THE INVENTION

Although the thermal conductivity detector system just described operates very well, a certain amount of noise at the switching frequency may be present in the output signal under conditions where there is a change in the difference between the mass flow of sample gas through the cavity of the cell and the mass flow of the reference gas. In accordance with this invention, this noise can be practically eliminated by ensuring that there is a significant difference in phase between the thermal conductivity component of the output signal of the cell that has just been described and a flow component of the output signal. The latter depends entirely on flow rate and is independent of the conductivity signal. The phase of the control wave of switching frequency that is applied to the synchronous detector is ideally made to be 90° out of phase with the flow signal so that the effect of the flow signal is cancelled by integration over a few switching cycles. This is possible because the switching frequency is higher than the highest frequency required to define the peaks.

THE DRAWINGS

FIG. 2 is a schematic diagram of a thermal conductivity detector system embodying the invention; and FIG. 2A is a schematic diagram illustrating a different way of incorporating a thermal conductivity cell into the system of FIG. 2.

Figure 1:
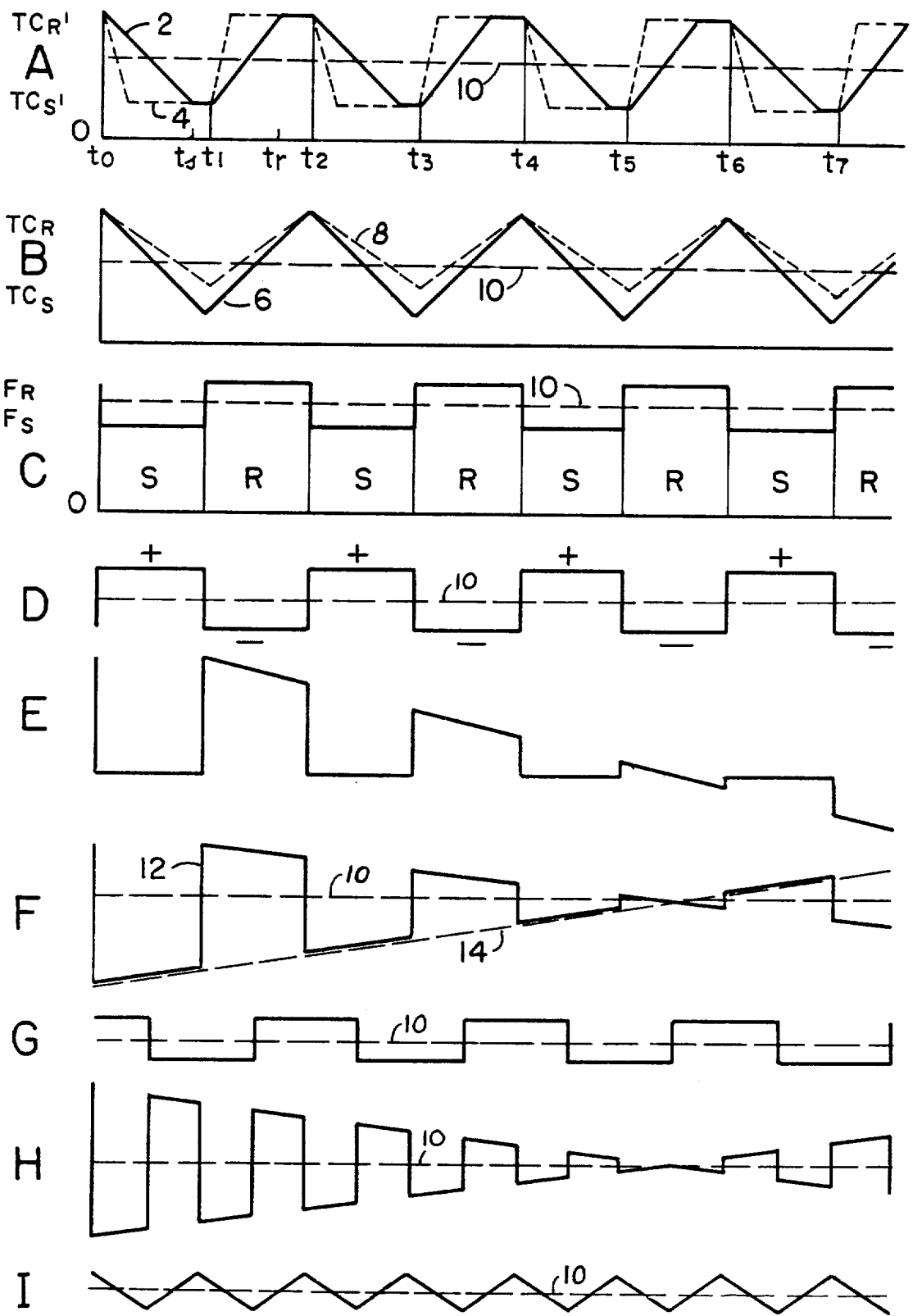
FIG. 1 is a series of graphs used in explaining the operation of a detector system incorporating the invention.

In order to maintain a filament having a resistance R at a constant temperature, the electrical power, $V^2/R$, supplied to the filament must equal the rate at which heat energy escapes from it. The voltage V is the output signal of the cell. The rate of heat loss has a thermal conductivity component and a flow component. The thermal conductivity component is the rate at which heat flows from the filament through the gas to the wall of the cell; and the flow component is the rate at which heat is carried out of the cell by the gas flowing through it. There is also a small constant rate of heat loss S that results from various causes. Thus, in order to keep the filament at a constant temperature, a voltage V must be applied to the filament such that $$V^2/R = G\lambda(T_f - T_w) + \dot{m}Cp(T_{out} - T_{in}) + S. \quad (1)$$

The first term is the thermal conductivity component in which G represents a geometric constant of the cell; $\lambda$ is the thermal conductivity of the gas in the cell; $T_f$ is the temperature of the filament; and $T_w$ is the temperature of the cell wall. The second term of the equation is the flow component in which $\dot{m}$ represents the mass flow rate of the gas through the cell; Cp is the specific heat of the gas; $T_{out}$ is the temperature of gas as it flows out of the cell; and $T_{in}$ is the temperature of the gas as it flows into the cell.

Thermal Conductivity Component of Rate of Heat Loss

At time $t_0$ in graph A of FIG. 1, it is assumed that the cavity of a thermal conductivity cell is full of reference gas and that the cavity is just being switched from a source of reference gas to the output of a column. At $t_0$, the thermal conductivity component $TC_R$ of equation (1) is $G\lambda_R(T_f - T_w)$ where $\lambda_R$ is the thermal conductivity component of the rate of heat loss due to reference gas. If the elutant from the column at $t_0$ is carrier gas having a thermal conductivity equal to that of the reference gas, the output voltage of the cell will not change, but if, as illustrated in graph A, the elutant is one of the sample gases having a degree of concentration such that its thermal conductivity, $\lambda_S$, is less that $\lambda_R$, the thermal conductivity component of the rate of heat loss will decrease at a rate determined by the rate at which the sample gas enters the cavity. The rate at which heat flows from the filament to the wall of the cavity is the sum of the rates at which heat flows through the sample and reference gases that are in it. If the flow rate of the sample gas is sufficient to fill the cavity before time $t_1$, when the cavity is again connected to the source of reference gas, the thermal conductivity component will drop to a value $TC_S$ which is equal to $G\lambda_S(T_f - T_w)$. It will remain at this value until $t_1$ when it will increase toward the value $TC_R$ at a rate determined by the rate at which reference gas flows into the cavity. Thus, the thermal conductivity component of the rate of heat loss of the cell will vary under the assumed conditions as indicated by the trapezoidal wave 2 in graph A. If the flow rates of the sample gas and reference gas into the cavity are increased, the trapezoidal wave will be advanced in phase as indicated by the dotted line 4.

If, on the other hand, the flow rates of the reference and sample gases into the cavity of the cell are reduced so that the cavity is not filled with either gas before it is switched to receive the other, the thermal conductivity component will be triangular in form as indicated at 6 in graph B of FIG. 1. As the flow rates are further decreased, the amplitude of the triangle reduces as indicated by the dotted line 8 of graph B in FIG. 1.

Flow Component of Rate of Heat Loss

If we assume that the specific heats $C_R$ and $C_S$ of the sample and reference gases are the same and that their densities are the same, the flow component of equation (1) will be zero if the volumetric flow rates $F_S$ and $F_R$ are the same. But if the flow of sample gas is always a given amount less than the flow of reference gas, the flow component of the rate of heat loss will appear as indicated in graph C of FIG. 1 wherein the letters S and R indicate which gas is flowing.

Output Signal

As previously stated, the output signal of the thermal conductivity cell is the voltage V required to maintain the filament at a constant temperature and, as can be seen from equation (1), it is proportional to the square root of the sum of the rates of heat loss due to thermal conductivity and flow. For simplicity of illustration, however, it will be assumed that the thermal conductivity and flow components of the output signal V are qualititative rather than quantitative in nature and that they correspond to the respective rates of heat flow of these components illustrated in the graphs A, B and C of FIG. 1.

Flow Component of Output Signal

With a constant difference between the flows $F_S$ and $F_R$, the flow signal component of the output voltage of a cell corresponds to the flow component of the rate of heat loss of graph C. When this voltage is AC coupled to one input of a synchronous detector, it will vary about the axis 10. If a control wave such as indicated at D of FIG. 1 that is in phase with the switching at the cell is applied to the other input of the synchronous detector, and if it is assumed that the wave D multiplies the AC wave C by $+1$ when it is positive and by $-1$ when it is negative, the net result will be a constant DC output of fixed offset which will not interfere with the measurement of peak areas in a GC system.

In practice, however, there is often a continuous change in one or both of the flow rates $F_S$ and $F_R$ due to programmed temperature changes in the oven containing the column into which the sample is injected and a column through which reference gas may flow before reaching the detector. The wave E of FIG. 1 illustrates the flow component of the output signal of a cell in which $F_R$ varies and $F_S$ is constant. When this signal is AC coupled to a synchronous detector, it will appear at the signal input of the synchronous detector as indicated by the wave 12 of graph F of FIG. 1. If this wave is multiplied in a synchronous detector with a control wave such as D that, as previously stated, is in phase with the switching at the cell, it will produce a wave indicated by the line 14 and introduce baseline variations into the desired signal at the output of the synchronous detector. Such variations could significantly interfere with peak area measurements in the GC system.

In accordance with this invention, however, the wave 12 is multiplied in the synchronous detector by a control wave G that is 90° out of phase with the switching at the cell. Once again, multiply by $+1$ when the wave G is in a high state and by $-1$ when it is in a low state. The result will be wave H. During each half-cycle of the wave G, the wave 12 changes signs, so that the wave H has positive and negative portions that nearly cancel each other to reduce the noise. What is left over appears at twice the switching frequency and can be removed by passing the signal H through a low pass filter or integrator. The output of the low pass filter is then free from flow interference.

Thermal Conductivity Component of the Output Signal

If a voltage corresponding to the triangular shaped wave 6 in the graph B of FIG. 1 is AC coupled to a synchronous detector, it will vary on either side of its AC axis 10. When multiplied by a wave like G that is 90° out of phase with the switching cycle, the result will be the double frequency wave I, the average value of which represents the thermal conductivity difference between sample and reference gas. It will be noted that if the control wave D were applied to the synchronous detector, the output would be zero.

In accordance with the discussion of the graphs A of FIG. 1, the thermal conductivity component of the signal may be made to have a trapezoidal shape such as indicated by the wave 2. By increasing the flow rates $F_S$ and $F_R$, it may be advanced in phase as indicated by the graph 4. If the phase advance is carried too far, as illustrated by the wave 4, multiplication in a synchronous detector with a control wave G would produce very little output. If the signal, such as the trapezoidal wave 2, were coupled to the synchronous detector, a useful output signal would be attained. It is therefore important that there be a significant difference between the phase of the thermal conductivity component and the phase of the flow component.

Embodiment of the Invention

In the chromatographic system schematically illustrated in FIG. 2, elutant from a column and reference gas are made available at respectively opposite ends of a thermal conductivity cell TC in the following manner. Detailed discussion of the manner in which the various valves v are opened and closed will not be presented, as it is obvious and not part of this invention. Carrier gas from a tank 20 is conducted via a variable mass flow control 22 to one end of a gas chromatographic column 24. Samples of a mixture of chemicals to be measured are inserted in the stream of carrier gas flowing to the column 24 by a sample injector 26. Elutants from the other end of the column 24 are conducted by a tube 28 to one end 29 of the cell TC. If carrier gas is to be used as reference gas, it can be conducted to the end 30 of the cell TC via a variable mass flow control 32, a chromatographic column 34, and a tube 36. Both columns 24 and 34 are contained in an oven 38, the temperature of which may be programmed in a manner schematically represented by a programmed temperature controller 39 and a heating resistor 40. Other means, such as controllable vents, may also be used to control temperature.

In a dual column system such as just described, the purpose of the column 34 is to introduce the same kind of "bleed" components into the gas passing through it as are introduced by the column 24, thereby making the gas applied to opposite ends of the cell TC as nearly alike as possible except for the gas constituents resulting from the introduction of the sample into the column 24. Single column operation can be attained by connecting mass flow control 32 directly to tube 36 as indicated by dotted lines 41. Alternatively, if it is desired to use a gas other than the carrier gas as a reference gas, it can be supplied from a source 42 to the input of mass flow control 32 in place of carrier gas, as indicated by dotted lines 45.

Switching the Flow in the Thermal Conductivity Cell

Control of the flow of reference gas from the tube 36 and column elutant from the tube 28 through the cell TC may be effected as follows. An oscillator 43 supplies square waves, indicated at O, having a frequency such as 20 Hz to the clock terminal of a D flip-flop 44. Its $\overline{Q}$ terminal is connected to its D teminal so that a 10 Hz square control wave CW is produced at its Q terminal. A 10 Hz square control wave $\overline{CW}$ that is 180° out of phase with the wave CW is produced at the $\overline{Q}$ terminal. Hence, the D flip-flop 44 operates to divide the frequency of the waves O by two and produce out-of-phase components thereof.

The terminal Q of the D flip-flop 44 is connected to the D terminal of another D flip-flop 46 so as to apply the 10 Hz wave CW thereto. The output of the oscillator 43 is coupled via an inverter 48 to the clock terminal of the D flip-flop 46 so as to apply a 20 Hz square wave O' thereto, the wave O' being 180° out of phase with the wave O. The result is that the D flip-flop 46 outputs at its $\overline{Q}$ terminal a switching control wave S of 10 Hz that is 90° out of phase with the waves CW and $\overline{CW}$.

The 10 Hz switching wave S is applied to the base of a transistor 50 having its emitter connected to ground and its collector connected to a point of positive voltage via a solenoid coil 52. When the wave S is positive, the solenoid coil 52 is energized and causes a member 54 contained in a chamber 56 to bear against and close an outlet port 58 of the chamber 56. When the coil 52 is not energized, spring means, not shown, move the member 54 to a position where it bears against and closes another outlet port 60 of the chamber 56. Switching gas from a source 62 is conducted into the chamber 56 via an inlet port 64. The port 58 is connected via a tube 66 to a point $J_1$ that is intermediate the end of a tube 68 that is connected to a vent 70 and the end joined to the cell TC at 29. Similarly, the port 60 is connected via a tube 72 to a point $J_2$ that is intermediate the end of a tube 74 that is connected to the vent 70 and the end joined to the cell TC at 30.

With the member 54 in the position shown, and during a positive half-cycle of the 10 Hz switching wave S, switching gas flows out the port 60 of the chamber 56 through the tube 72 to the point $J_2$ in the tube 74. Because of the hydraulic resistances in the flow path to the vent 70, a pressure $P_2$ can be created at $J_2$ that prevents reference gas in the tube 36 from flowing to the vent 70 via the tube 74 and causes it to flow through the cell TC and to the vent 70 via the tube 68. Sample gas in the tube 28 does not enter the cell TC but passes to the vent 70 via the tube 68. During the negative half-cycle of the switching wave S, the member 54 blocks the port 60 so that switching gas flows out of the port 58 and through the tube 66 to the point $J_1$. This creates a pressure $P_1$ at $J_1$ that prevents sample gas in the tube 28 from entering the tube 68 and causes it to flow through the cell TC and to the vent 70 via the tube 74. In this particular embodiment, the reference gas and sample gas flow through the cell TC in opposite directions. But even if the hydraulic arrangement were such that both sample gas and reference gas flowed through the cell in the same direction, the voltage signal would be essentially the same.

The Filament Circuit

As previously stated, the output signal of the cell TC is the voltage necessary to maintain the temperature or resistance of its filament F constant. The filament F is connected in a bridge circuit including resistors $R_1$, $R_2$ and $R_3$. The diagonal point of the bridge where the filament F joins the resistor $R_3$ is connected to ground; and the opposite diagonal point, there $R_1$ joins $R_2$, is connected to the emitter of an NPN transistor 78. Its collector is connected to a point of positive voltage. The emitter of an NPN transistor 80 is connected to the base of the transistor 78, and the collector of the transistor 80 is connected to the collector of the transistor 78, forming a Darlington pair. The diagonal point of the bridge where the filament F joins the resistor $R_1$ is connected to the inverting input of an operational amplifier 82; and the opposite diagonal point, where the resistor $R_2$ joins the resistor $R_3$, is connected to the non-inverting input of the amplifier 82. The output of the amplifier 82 is connected to the base of the transistor 80.

The values of resistors $R_1$, $R_2$ and $R_3$ are chosen so that the bridge will be in balance for a particular predetermined value of filament resistance corresponding to a particular filament temperature. The operational amplifier 82 in combination with the Darlington-connected transistors 80 and 78 adjust the voltage V at the diagonal point where $R_1$ joins $R_2$ to provide the amount of current through the filament F which will heat it to the above-mentioned temperature, keeping the bridge in balance. Presence of sample gas in the cell 30 with thermal conductivity lower than that of carrier or reference gas will tend to cause the filament F to rise above its operating temperature and increase its resistance. This increase in resistance of the filament F increases the voltage at the bridge diagonal where the filament F joins resistor $R_1$. The output of the operational amplifier 82 decreases in response to the application of voltage to its inverting input terminal and reduces the drive to the Darlington transistors 78 and 80. This, in turn, reduces the voltage V at the top diagonal point of the bridge and reduces the current through filament F. The temperature and resistance of the filament F drop back to the operating values. The bridge balance is thus restored and constant filament temperature operation is attained. The voltage V at the point where $R_1$ and $R_2$ join is the output signal of the cell.

Synchronous Detector

Before the signal V is applied to a synchronous detector, it is AC coupled via a capacitor 84 to the non-inverting input of an operational amplifier 86. A resistor 88 is connected between that input and ground. The capacitor 84 and the resistor 88 advance the phase of the signal V. The output of the amplifier 86 is connected to ground via series resistors 90 and 92, and their junction is connected to the inverting input. Attenuation of line and other higher frequencies is attained by connecting a capacitor 94 in shunt with the resistor 90.

The output of the amplifier 86 is applied to the input 96 of a synchronous detector 98. The synchronous detector 98 may take many forms, but as illustrated, it is comprised of two parallel branches. One branch includes a capacitor 100, a resistor 102, and the source-drain path of a FET 104 connected in series between the input 96 and an output 106 and a FET 108 having its source-drain path connected between the ground and the junction of the resistor 102 and the FET 104. The other parallel branch includes an inverting unity gain amplifier 110, a capacitor 112, a resistor 114, and the source-drain path of a FET 116 connected in series between the input 96 and the output 106 with the source-drain path of a FET 118 connected between ground and the junction of the resistor 114 and the FET 116. As indicated, the voltage of control wave CW is applied to the gate of the FET 104 and to the gate of the FET −18; and the voltage of control wave $\overline{CW}$ is applied to the gate of the FET 108 and to the gate of the FET 116. When the voltage applied to the gate of a FET is positive, its source-drain path has very little resistance; and when the voltage is negative, the source-drain path has a high resistance.

The output 106 of the synchronous detector 98 is connected to a low pass filter 120 that cuts off at about 1 Hz so as to severely attenuate the switching frequency of 10 Hz. Although any suitable form of filter may be used, the low pass filter 120 is illustrated as being comprised of an operational amplifier 122 having its non-inverting input connected to ground, its inverting input connected to the output 106 of the synchronous detector 98, and its output connected to its inverting input via a capacitor 124 shunted by a resistor 126. The desired output signal of the system is present at the output of the amplifier 122 and is free from switching noise.

Operation of FIG. 2

As discussed in connection with the graphs A and B of FIG. 1, the output signal V of the cell TC may be trapezoidal or triangular in shape depending on the flow rate of the reference gas in the tube 36 of FIG. 2 and the flow rate of the sample gas in the tube 28. It was explained that noise otherwise caused by the presence of a flow component such as shown at E in FIG. 1 can be eliminated if it is multiplied in the synchronous detector by a wave such as shown at G that is 90° out of phase with it. It was also shown that the desired thermal conductivity component of the output signal V must have a phase relationship other than 90° with the wave G at the input of the synchronous detector 98 if any useful output is to be attained.

The flow component of the output signal V of the cell will be in phase with the actual switching between the flow of reference gas and sample gas into the cell TC at its ends 30 and 29 respectively. If this component is to arrive at the input 96 of the synchronous detector 98 in phase quadrature with the control wave voltages CW and $\overline{CW}$, it must be in phase with the switching voltage S. For this to occur, it is required that the total delay, whether hydraulic or electrical, between the point of application of the switching wave S, which is at the base of the transistor 50, and the input 96 of the synchronous detector 98 be near zero. It is apparent that, if the total delay were not near zero, this could be compensated for by changing the phase relationship between the switching wave S and the control waves CW and $\overline{CW}$ to something other than 90° or by choosing electrical component values in the circuit to compensate for hydraulic and mechanical delays and create a near-zero phase shift of the flow component as detailed above.

The thermal conductivity component is phase-shifted from the flow component by the action of the flow switching, as shown in the graphs of FIG. 1, such that the synchronous detector rejects the flow component and produces an output proportional to the thermal conductivity component.

One-Way Flow through the TC Cell

FIG. 2A illustrates the hydraulic coupling for a thermal conductivity cell in the system of FIG. 2 in which the sample gas from the tube 28 and the reference gas from the tube 36 flow through a thermal conductivity cell in the same direction rather than opposite directions as in the coupling arrangement of FIG. 2. Two solenoid valves 128 and 130 are provided. The tube 36 conducts reference gas into the cavity of the valve 128, and the tube 28 conducts sample gas into the cavity of the valve 130. Solenoids 132 and 134 are connected in series with the collector-emitter path of a transistor 136, and the wave S of FIG. 2 is applied to its base. When the wave S is positive, current flows through the solenoids 132 and 134 and moves members 136 and 138 that are respectively contained in the cavities of the valves 128 and 130 to the left. In this position, the member 136 blocks a venting port 140 for the cavity of the valve 128 so that reference gas flows through the cavity to an output port 142 that is connected to a tube 144. The member 138 blocks an output port 146 that is connected to a tube 148 so that sample gas from the tube 28 flows through the cavity of the valve 130 and out its venting port 150. During the negative portion of the wave S, the solenoids 132 and 134 are not energized and spring means, not shown, move the members 136 and 138 to the right so that they block the ports 142 and 150 respectively. In this position, sample gas from the tube 28 flows through the port 146 into the tube 148 and reference gas from the tube 36 flows out the venting port 140.

The tubes 144 and 148, through which reference gas and sample gas alternately flow as a result of the action just described, are connected to a tube 152 having a trombone section 154 so that the length of the tube 152 can be varied. One end of a thermal conductivity cell TC' is connected to the tube 152 as shown so that the alternate flows of reference and sample gas from the tubes 144 and 148 respectively flow in the same direction past the filament F'. After passing through the cell TC', the gases exit from a port 156 which may be connected to a vent or to other parts of the chromatograph system, as desired.

In the hydraulic arrangement shown in FIG. 2, the switching of the reference gas and sample gas respectively takes place at the ports 30 and 29 at the ends of the cell TC. Under this condition, the thermal conductivity signal of the wave A of FIG. 1 and the flow signal of the wave C will have the phase relationships previously discussed. The phase relationships may be different in the apparatus of FIG. 2A because of the variable effective length of the tubing provided by the trombone section 154 of the tube 152. The trombone section 154 may be adjusted so as to make the phase difference between the thermal conductivity and flow components of the signal provided by the cell TC' to be sufficiently close to 90° to ensure the recovery of an adequate signal by the synchronous detector 98. In FIG. 2, the phase relationships between a thermal conductivity component and a flow component are determined by the time it takes for the sample and reference gases to flow through the cell because the switching points are at the ends of the cell, but in FIG. 2A the phase relationships are also affected by the length of tubing between the junction J₃ where the tubes 144 and 148 intersect and the input of the thermal conductivity cell TC'.

This results from the fact that the differences in flow rates of sample and reference gases cause an almost immediate effect in the flow component of the signal V when the valves switch and from the fact that the effect on the thermal conductivity component is delayed by the transit time of the gas components through the tubes 152. In this system the switching point would be the junction J₃ of the tube 144, the tube 148 and the tube 152. The length of the tubes 144 and 148 would have negligible effect as they are always full of reference and sample gas respectively and have negligible hydraulic pressure delays.

What is claimed is:

1. In a gas chromatograph,
a chromatographic column,
a source of reference gas,
a thermal conductivity detector,
means for alternately switching said thermal conductivity detector between the output of said column and the output of said source of reference gas at a given switching frequency so as to produce an output signal that may have a flow component in phase with said switching frequency, the flow rates of said sample gas and reference gas being such as to produce a thermal conductivity component in said output signal that is not in phase with the switching frequency,
means providing a control signal having said switching frequency,
a synchronous detector,
means coupling said output signal of said thermal conductivity detector to said synchronous detector, and
means coupling said control signal to said synchronous detector in such manner that it is in or near phase quadrature with the flow component of the output signal.

2. In a gas chromatograph capable of supplying reference gas and sample gas to first and second points respectively, the combination comprising
a thermal conductivity cell having an input,
means for alternately connecting the input of said cell to said first and second points at a given switching frequency so as to produce an output signal at said frequency having a flow component and a thermal conductivity component in or near phase quadrature with each other,
a synchronous detector having first and second inputs and an output,
means for alternating current coupling said output signal of said cell to said first input of said synchronous detector,
means for deriving an alternating control signal of said switching frequency such that said control signal is in or near phase quadrature with the flow component of said output signal of said thermal conductivity cell, and
means for coupling said control signal to said second input of said synchronous detector.

3. In a gas chromatograph, the combination comprising
first hydraulic coupling means for the input of a chromatographic column,
second hydraulic coupling means for the output of a chromatographic column,
a point to which a source of reference gas may be coupled,
third hydraulic coupling means for coupling to the cavity of a thermal conductivity cell,
hydraulic switching means for alternatively coupling said third hydraulic coupling means to said second hydraulic coupling means and to said point,
circuit means for providing a voltage required to maintain the filament of a thermal conductivity cell, when present, at a constant temperature,
a synchronous detector having first and second inputs and an output,
a source of a control wave that is in phase quadrature with the switching performed by said hydraulic switching means,
means coupling said control wave to one of said first inputs of said synchronous detector, and means alternating current coupling the voltage provided said circuit means to said second input of said synchronous detector.

4. Detecting apparatus, comprising a thermal conductivity cell having a cavity therein and producing a signal at its output containing a thermal conductivity component and a flow component, switching means having a first input to which reference gas may be applied, a second input to which sample gas may be applied, an output, and means for selectively connecting either of said first and second inputs to said output of said switching means, means coupling the output of said switching means to the cavity of said thermal conductivity cell, means for producing a control signal having a given frequency, means responsive to said control signal for causing said switching means to alternate the connection of its first and second inputs to its output once each cycle of said given frequency, a synchronous detector having two inputs and an output, and means respectively coupling said inputs of said synchronous detector to the output of said thermal conductivity detector and to the means for producing the control signal such that the latter is 90° out of phase with the flow component in the signal derived from said thermal conductivity detector as said component appears at the input of said synchronous detector.

* * * * *